(12) United States Patent
Renard et al.

(10) Patent No.: US 7,478,850 B2
(45) Date of Patent: Jan. 20, 2009

(54) OCULAR DEVICE

(75) Inventors: Jerome Renard, Beverly Hills, CA (US); Mathieu Lion, Paris (FR)

(73) Assignee: Lomdom, SAS, Paris (FR)

( * ) Notice: Subject to any disclaimer, the term of this patent is extended or adjusted under 35 U.S.C. 154(b) by 183 days.

(21) Appl. No.: 11/435,113

(22) Filed: May 15, 2006

(65) Prior Publication Data

US 2007/0262596 A1    Nov. 15, 2007

(51) Int. Cl.
*A61F 9/00* (2006.01)
(52) U.S. Cl. .......................................... 294/1.2; 606/107
(58) Field of Classification Search ................. 294/1.2; 606/107

See application file for complete search history.

(56) References Cited

U.S. PATENT DOCUMENTS

| | | | |
|---|---|---|---|
| 1,316,436 A | 9/1919 | Feeney | |
| 1,667,552 A | 4/1928 | Igou | |
| 2,224,575 A | 12/1940 | Montalvo-Guenard | |
| 2,379,629 A | 7/1945 | Eweson | |
| 2,384,334 A | 9/1945 | Olson | |
| 2,919,696 A | 1/1960 | Rinaldy | |
| 3,031,918 A | 5/1962 | Moyers | |
| 3,091,328 A | 5/1963 | Leonardos | |
| 3,129,971 A | 4/1964 | Kobler | |
| 3,132,887 A | 5/1964 | Martinez | |
| 3,139,298 A | 6/1964 | Grabiel | |
| 3,177,874 A | 4/1965 | Spriggs | |
| 3,411,364 A | 11/1968 | Horley et al. | |
| 3,424,486 A | 1/1969 | Corley | |
| 3,490,806 A | 1/1970 | Lopez-Calleja et al. | |
| 3,584,908 A | 6/1971 | Ray | |
| 3,600,028 A | 8/1971 | Henning | |
| 3,645,576 A | 2/1972 | Horres | |
| 3,647,380 A | 3/1972 | Middleton | |
| 3,697,109 A * | 10/1972 | Parrent | ........................ 294/1.2 |
| 3,769,963 A | 11/1973 | Goldman et al. | |
| 3,791,689 A | 2/1974 | Boone et al. | |
| 3,879,076 A | 4/1975 | Barnett | |
| 3,922,025 A * | 11/1975 | Updegraff | ................... 294/1.2 |
| 3,934,914 A | 1/1976 | Carruthers | |
| 3,971,270 A | 7/1976 | Wallace | |
| 4,026,591 A | 5/1977 | Cleveland | |
| 4,037,866 A | 7/1977 | Price | |
| 4,042,999 A | 8/1977 | Triantafyllou | |
| 4,047,532 A | 9/1977 | Phillips et al. | |
| 4,071,272 A | 1/1978 | Drdlik | |
| 4,079,976 A | 3/1978 | Rainin et al. | |
| 4,082,339 A | 4/1978 | Ross | |
| 4,088,359 A | 5/1978 | Buchanan, Jr. | |
| 4,093,291 A | 6/1978 | Schurgin | |
| 4,097,081 A | 6/1978 | England | |
| 4,113,297 A | 9/1978 | Quinn | |

(Continued)

*Primary Examiner*—Dean J Kramer
(74) *Attorney, Agent, or Firm*—Connolly Bove Lodge & Hutz LLP

(57) ABSTRACT

An ocular device to facilitate the positioning and insertion of an object onto a subject's eyes having a base comprising a mouthpiece and at least one support coupled to the base. The support is displaced at a distance measured from the mouthpiece to the area in front of the center of the subject's eye when the mouthpiece is placed between the subject's teeth. The support is configured to releasably retain the object, such as a contact lens. The ocular device may further be provided with receptacle heads that accommodate medication to be administered to the subject's eyes.

62 Claims, 13 Drawing Sheets

U.S. PATENT DOCUMENTS

| | | |
|---|---|---|
| 4,123,098 A | 10/1978 | Shoup |
| 4,126,345 A | 11/1978 | List |
| 4,167,283 A | 9/1979 | Feldman |
| 4,190,277 A | 2/1980 | England |
| 4,192,204 A | 3/1980 | Feldman |
| 4,193,622 A | 3/1980 | Overman |
| 4,200,320 A | 4/1980 | Durham |
| 4,201,408 A | 5/1980 | Tressel |
| 4,221,414 A | 9/1980 | Schrier |
| 4,238,134 A | 12/1980 | Cointment |
| 4,244,466 A | 1/1981 | Arnhem |
| 4,263,054 A | 4/1981 | Giambalvo |
| 4,269,306 A | 5/1981 | Feniger |
| 4,286,815 A | 9/1981 | Clark |
| 4,326,742 A | 4/1982 | Ingram |
| 4,332,318 A | 6/1982 | Feldman |
| 4,332,408 A | 6/1982 | Cointment |
| 4,337,858 A | 7/1982 | Thomas et al. |
| 4,357,173 A | 11/1982 | Rosenthal et al. |
| 4,378,126 A | 3/1983 | Procenko |
| 4,387,921 A | 6/1983 | Licata |
| 4,415,076 A | 11/1983 | Campbell |
| 4,479,672 A | 10/1984 | Jermyn |
| 4,512,601 A | 4/1985 | Jacobstein |
| 4,512,602 A | 4/1985 | England |
| 4,527,824 A | 7/1985 | Rosenfeld |
| 4,565,396 A | 1/1986 | Larimer |
| 4,703,964 A | 11/1987 | Ranani |
| 4,750,771 A | 6/1988 | Emmett et al. |
| 4,753,470 A | 6/1988 | Menard |
| 4,763,650 A | 8/1988 | Hauser |
| 4,964,663 A | 10/1990 | Jermyn |
| 4,986,586 A | 1/1991 | Eilrich et al. |
| 5,050,918 A | 9/1991 | Kolze |
| 5,069,494 A | 12/1991 | Reinson et al. |
| 5,184,405 A | 2/1993 | Cress |
| 5,192,070 A | 3/1993 | Nagai et al. |
| 5,236,236 A | 8/1993 | Girimont |
| 5,246,259 A | 9/1993 | Hellenkamp et al. |
| 5,348,358 A | 9/1994 | Selick |
| 5,407,241 A | 4/1995 | Harrison |
| 5,456,508 A | 10/1995 | Kozar |
| 5,474,349 A | 12/1995 | Selick |
| 5,496,084 A | 3/1996 | Miralles Medan |
| 5,511,752 A | 4/1996 | Trethewey |
| 5,538,301 A | 7/1996 | Yavitz et al. |
| 5,558,374 A | 9/1996 | Harrison |
| 5,649,727 A | 7/1997 | St. Louis |
| 5,662,659 A | 9/1997 | McDonald |
| 5,688,007 A | 11/1997 | Jefferson |
| 5,695,049 A | 12/1997 | Bauman |
| 5,785,370 A | 7/1998 | Pomerantz |
| 5,788,706 A | 8/1998 | Deminski |
| 5,879,038 A | 3/1999 | Morgan |
| 5,913,556 A | 6/1999 | Perusse |
| 5,941,583 A | 8/1999 | Raimondi |
| 6,030,013 A | 2/2000 | Fruhling et al. |
| 6,048,011 A | 4/2000 | Fruhling et al. |
| 6,168,638 B1 | 1/2001 | Kasim et al. |
| 6,358,288 B1 | 3/2002 | Kasim et al. |
| 6,398,277 B1 | 6/2002 | McDonald |
| 6,401,915 B1 | 6/2002 | Faxe |
| 6,502,876 B1 | 1/2003 | Stockhorst et al. |
| 6,572,165 B2 | 6/2003 | Faxe et al. |
| 6,602,266 B1 | 8/2003 | Loomas et al. |
| 6,632,232 B1 | 10/2003 | Loomas et al. |
| 6,637,881 B1 | 10/2003 | Siminou |
| 6,702,348 B1 | 3/2004 | Rigdon |
| 6,739,636 B2 | 5/2004 | Py |

\* cited by examiner

OCULAR DEVICE

FIELD OF THE INVENTION

The present invention relates generally to optometry and, more particularly, to devices and methods for the positioning and insertion of objects and fluids, such as contact lens, medication, and the like, onto a subject's eyes.

BACKGROUND OF THE INVENTION

Individuals who use contact lenses must regularly perform the task of placing a contact lens onto each eye. The most common method of inserting a contact lens involves placing a contact lens on the fingertip, properly positioning the contact lens on the fingertip in front of the eye, and placing the contact lens on top of the eye while keeping the eyelids open.

There are numerous drawbacks to this method. It is often difficult to correctly position the contact lens in front of the receiving eye. When the finger supporting the contact lens is brought close to the eye, there is a loss of focus and the image of the finger obscures the image of the lens. Moreover, the traditional method of inserting contact lens often requires the use of both hands: the finger of one hand to support and insert the contact lens onto the eye and the fingers of the other hand to prop open the eyelids of the receiving eye. Accordingly, good manual dexterity and coordination is required for the successful insertion of the contact lens onto the eye.

In view of the difficulties with respect to the proper positioning and insertion of contact lens, it is not surprising that many people are discouraged from wearing contact lens and instead choose to wear eye glasses. There are numerous devices that are directed to the handling and insertion of contact lens onto the wearer's eyes. However, there exists a need for a device that also provides stable, accurate and reproducible positioning and insertion of the contact lens onto the eyes.

The very same problems described above with respect to the placement and insertion of contact lens also arise in connection with the administration of medication onto the eyes. It is very difficult to accurately place medication, such as eye drops or creams, onto one's own eye. This is particularly true for the elderly and for people who have shaky hands. Contamination of the medication must also be avoided by preventing the medication container from contacting the eye or the surrounding tissues. There is thus a need for a device that provides accurate and reproducible application of medication and other objects onto the eyes.

BRIEF SUMMARY OF THE PREFERRED EMBODIMENTS

Devices and methods are disclosed for the positioning and insertion of objects, such as contact lens and medication, onto a subject's eyes. Although the devices and methods are disclosed herein with respect to the insertion of contact lens and medication, it is understood that the same devices and methods may also be used where it is desirable to position and/or insert any other objects or fluids onto the eyes.

There are many problems associated with inserting objects onto one's own eyes. Chief among the problems is the proper positioning of the object prior to insertion onto the eyes. It is not uncommon for several failed attempts to be made before the proper position is determined for successful insertion onto the eyes.

The ocular devices disclosed herein address the problems associated with determining the proper position of an object for placement onto the eyes by using the fixed distance between a person's bite and the eyes. The ocular devices use the subject's bite as the reference or anchoring point. The object to be inserted onto the subject's eye is then positioned at a distance from the subject's bite in an area substantially in front of the subject's eyes. Because the distance between the subject's bite and the subject's eye is fixed, it is possible to position an object for proper placement onto a person's eyes with greater reproducibility and accuracy by using the subject's bite as the reference point to place an object in front of the subject's eyes.

Accordingly, the ocular devices disclosed herein may be configured for a person's unique facial dimensions, which includes but is not limited to, a first and second distance between the subject's bite and each eye and a third distance between the subject's eyes. A fourth distance between the supports and the subject's face may be adjusted taking into consideration the extent to which the subject's bite is displaced relative to the subject's eyes along the vertical plane of the subject's face.

In accordance with one preferred embodiment, an ocular device to facilitate the positioning and insertion of an object onto a subject's eyes is disclosed. In this preferred embodiment, the ocular device comprises a mouthpiece that is held between the subject's teeth and two supports coupled to the mouthpiece and removably retaining the object to be inserted onto the subject's eyes. The mouthpiece anchors and stabilizes the location of the two supports relative to the subject's eyes. Moreover, the supports are positioned at a distance from the mouthpiece that is at least partially in front of the subject's eyes when the mouthpiece is held between the subject's teeth.

In accordance to another preferred embodiment, an ocular device to facilitate the positioning and insertion of an object onto a subject's eyes is disclosed. The ocular device comprises a base having a mouthpiece and at least one support coupled to the base and configured to releasably retain the object. The support is positioned at a distance from the base when the mouthpiece is placed between the subject's teeth such that displacement of the support toward the subject's eyes places the object onto the subject's eyes.

In accordance with yet another preferred embodiment, the ocular device comprises a base, at least one support, and an expandable chamber assembly coupled to the support. The expandable chamber assembly expands to urge the support toward the subject's eyes to insert the object onto the subject's eyes when pressure is applied to the expandable chamber assembly.

In accordance with a further preferred embodiment, the ocular device comprises a base comprising a mouthpiece and at least one inlet hole disposed in the mouthpiece. The ocular device further comprises first and second supports each having an expandable chamber in fluid communication with the at least one inlet hole. The first and second supports are actuated towards the subject eyes when air is blown into the inlet hole.

In accordance with still a further preferred embodiment, the ocular device is used to facilitate the administration of medication onto the subject's eyes. In this further preferred embodiment, the ocular device comprises a base having a mouthpiece and at least one receptacle head configured to store medication. The receptacle head is positioned at a distance from the base and substantially in front of the subject's eyeball when the mouthpiece is placed between the subject's teeth.

In accordance with yet a further preferred embodiment, the ocular device to facilitate the positioning and insertion of an object onto a subject's eyes. The ocular device comprises a mouthpiece means held in position in the subject's bite, a support means for releasably maintaining an object to be inserted onto the subject's eyes, and an actuating means for displacing the support means towards the subject's eyes to insert the object onto the subject's eyes. The mouthpiece means provides a stable anchoring point and the support means are positioned at a distance from the mouthpiece means to reproducibly insert the object onto the subject's eyes when the actuating means displaces the support means towards the subject's eyes.

Also disclosed are methods for inserting an object onto the eyes. The method comprises providing the ocular insertion device disclosed herein, placing the object to be inserted onto the eyes on the support, biting the mouthpiece, and causing the support to actuate towards the eyes to contact the object onto the eyes. The mechanism by which the support is actuated towards the eyes depends on the particular ocular device used.

In one aspect of the preferred embodiment, an ocular device with arms coupling the support to the base is used with the method. The support may be actuated towards the eyes by manually pushing the support towards, and inserting the object onto, the subject's eyes.

In another aspect of the preferred embodiment, an ocular device with an expandable chamber assembly is used with the method. Pressure may be applied to the expandable chamber assembly to actuate the supports towards, and inserting the object onto, the subject's eyes.

In a further aspect of the preferred embodiment, an ocular device with an inlet hole disposed in the mouthpiece is used. The object is placed onto the eyes by blowing air into the inlet holes and actuating the supports towards, and inserting the object onto, the eyes.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Although specific embodiments of the present invention will now be described with reference to the drawings, it should be understood that such embodiments are by way of example only and merely illustrative of, but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1A:
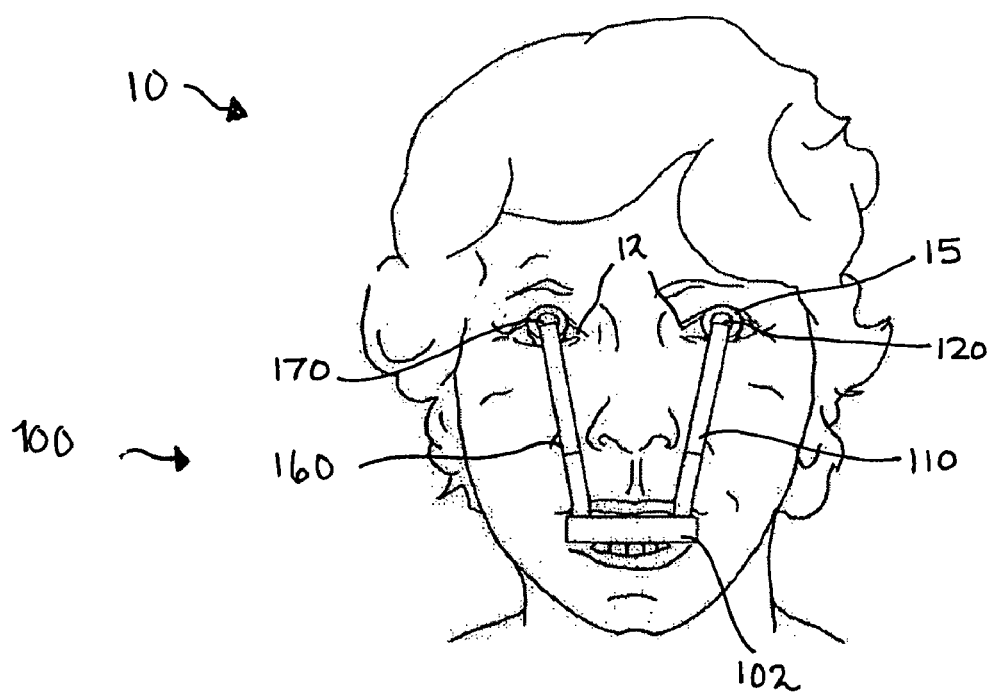
FIG. 1A is a front view of a subject's face showing the positioning of a preferred embodiment of the ocular device in use when placed in the subject's mouth.
Figure 1B:
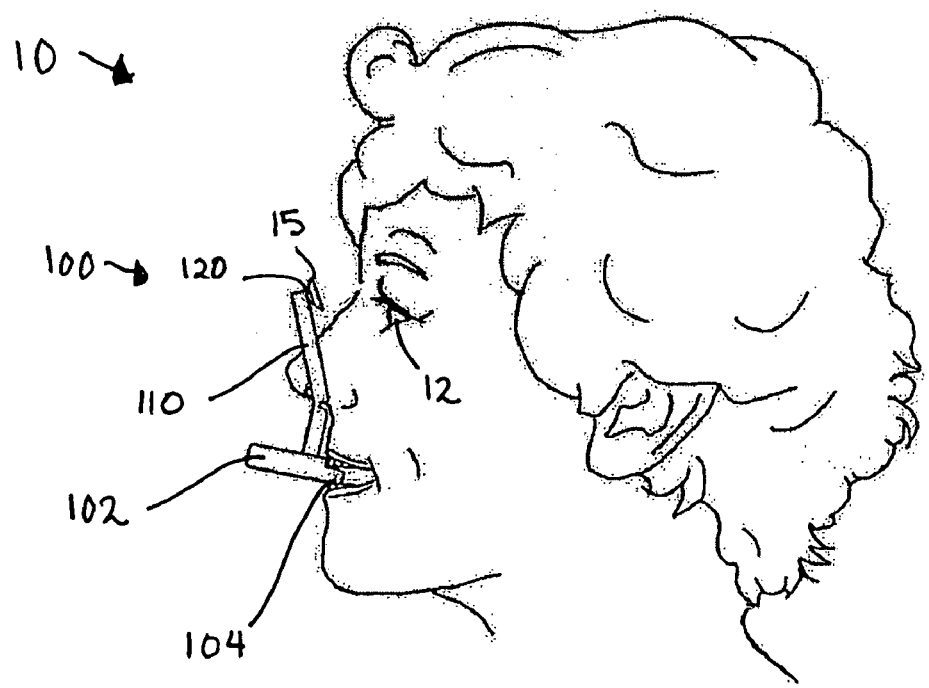
FIG. 1B is a side view of a subject's face and the preferred embodiment as shown in FIG. 1A.

FIGS. 1A-B illustrate a preferred embodiment of the ocular insertion device (100) positioned relative to the subject's face (10) for insertion of an object (15) retained on the supports (120, 170) onto the subject's eyes (12). As shown in FIGS. 1A-B, the distances between the subject's bite and the each of the subject's eyes is fixed.

The ocular insertion device (100) generally comprises a base (102) with a mouthpiece (104), a pair of arms (110, 160), and a pair of supports (120, 170) disposed on top of the arms (110, 160). The supports (120, 170) each removably support an object (15) that is intended for insertion onto the subject's eyes (12), such as a contact lens.

In a particularly preferred embodiment, the ocular device (100) is configured for each subject's unique facial dimensions, including the vertical distance between the subject's bite and each of the subject's eyes and the horizontal distance between the subject's eyes. The distance of the supports (120, 170) away from the subject's face (10) may also be adjusted depending on the extent to which the subject's bite and eyes are displaced along the vertical plane of the subject's face.

Once the ocular device (100) is configured for a particular subject's facial dimensions, the ocular device (100) provides consistently reproducible placement of any object that is supported on the supports (120, 170) onto the subject's eyes (12).

In this particularly preferred embodiment, the mouthpiece (104) is made of a material that is capable of retaining an impression of the subject's bite. The impression will ensure that the subject's bite is oriented in the same position on the mouthpiece (104) upon subsequent use. This, in turn, will ensure that the position of the supports (120, 170) relative to the subject's face remains consistent when the subject fits the bite onto the impression and provide reproducible positioning and insertion of the object (15) onto the subject's eyes. Non-limiting examples of materials suitable for the mouthpiece (104) include theromoelastomer plastic and other impressionable material.

Once an impression of the subject's bite is made on the mouthpiece (104), the vertical distance between the supports (120, 170) and the base (102), the horizontal distance between the supports (120, 170), and the distance between the supports (120, 170) from the subject's face (10) may be adjusted such that displacement of the supports (120, 170) in a direction toward the subject's face (10) will cause the object

(15) that is removably retained on the supports (120, 170) to be accurately positioned and placed on top of the subject's eyes (12).

In another preferred embodiment, the mouthpiece may comprise a pre-formed groove that is removably attached to the base. The pre-formed groove may be shaped in any number of ways that stabilizes the subject's bite on the mouthpiece. In one preferred embodiment, the pre-formed groove may be shaped in an arch that coincides with the arch of the subject's upper front teeth. Several mouthpieces having arch-shaped grooves of varying curvatures may be provided to accommodate the arch-shape of a particular subject's bite.

It is understood that while the supports (120, 170) may be positioned directly in front of the subject's eyes, this is not required in embodiments, such as the one depicted in FIGS. 1A-B, where a portion of the arms (110, 160) and the supports (120, 170) are angularly displaced.

Figure 2:
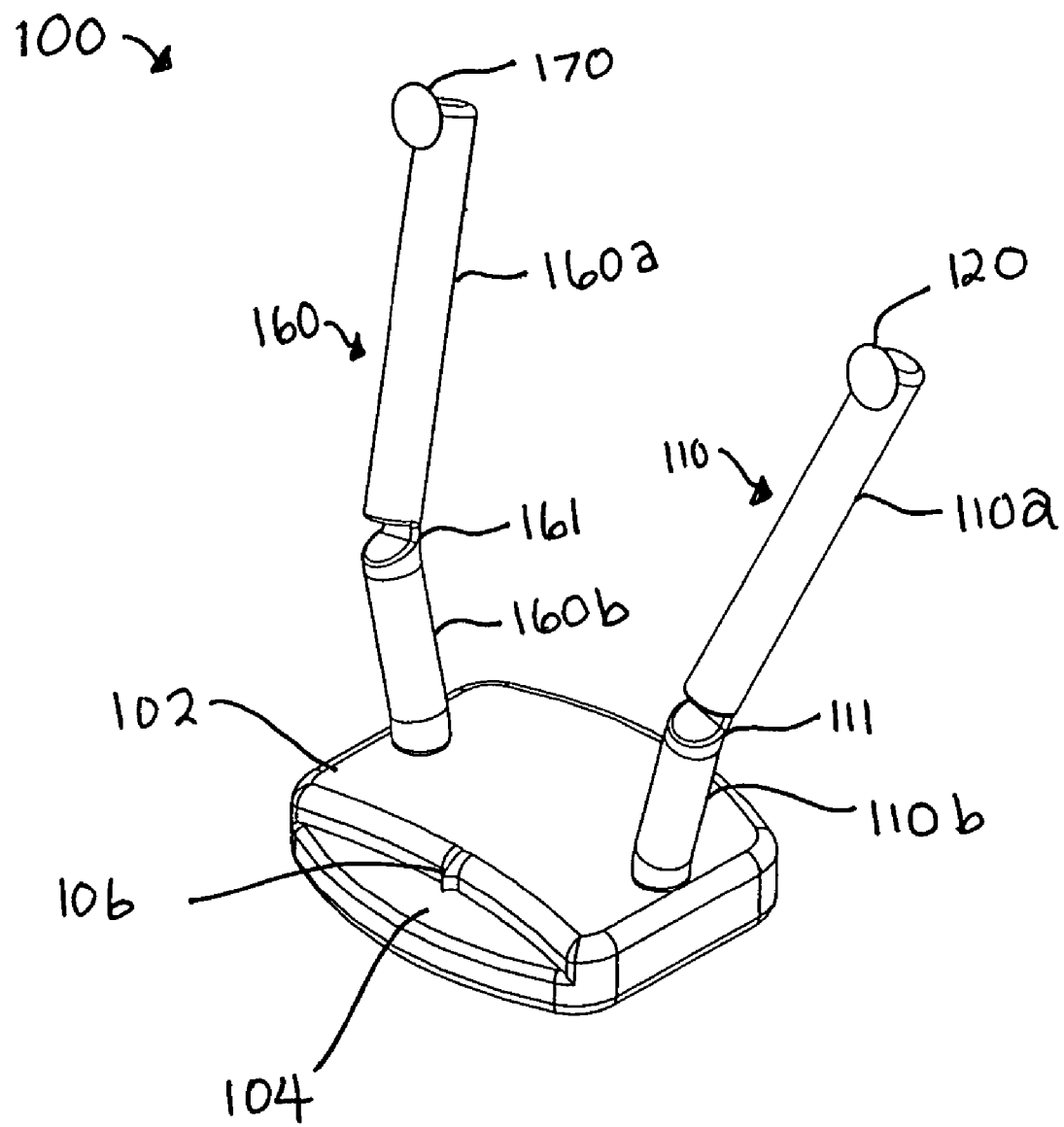
FIG. 2 is a perspective view of one preferred embodiment of the ocular device.
Figure 3:
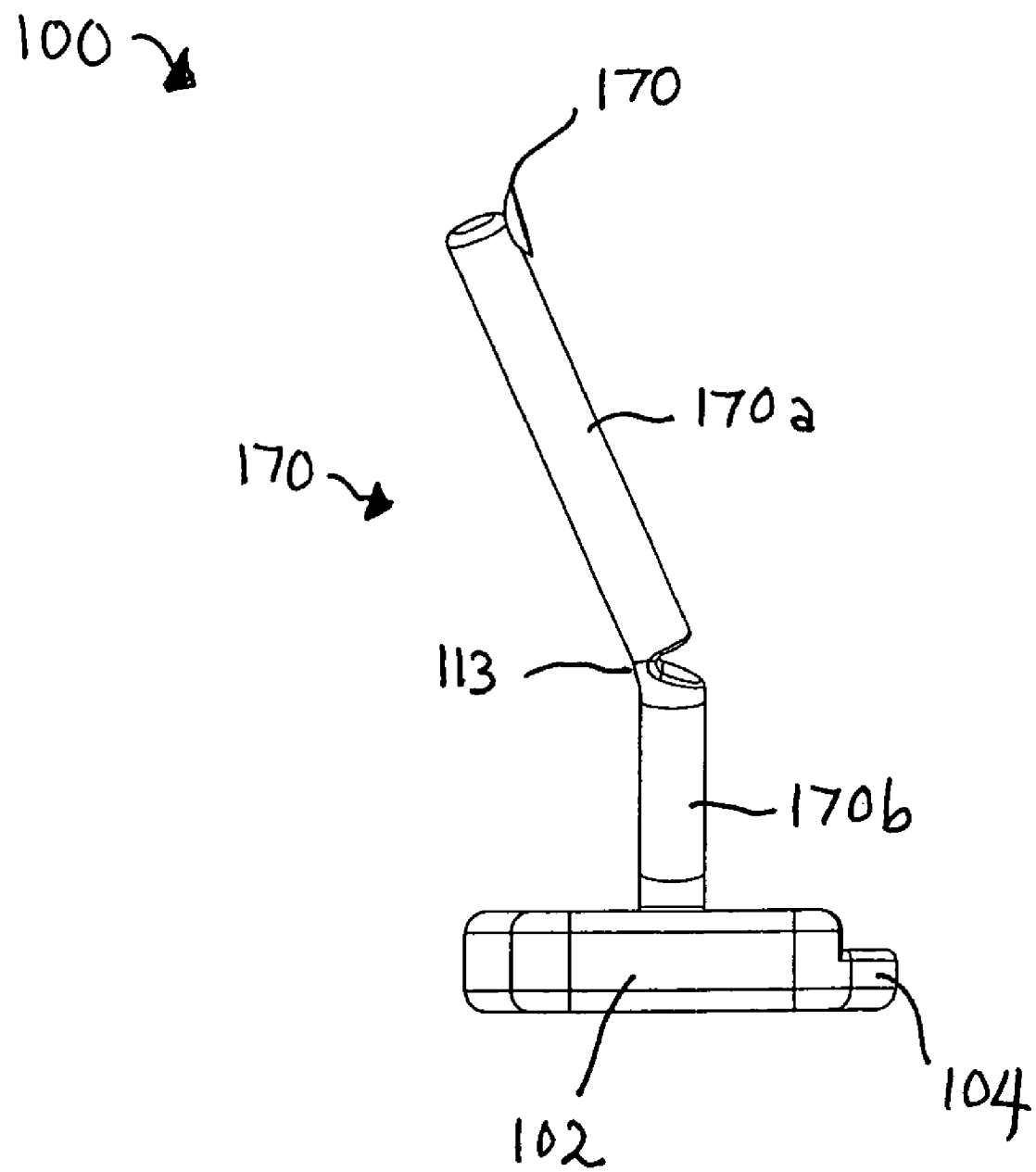
FIG. 3 is a side view of the preferred embodiment of the ocular device of FIG. 2.

FIGS. 2-3 illustrate a preferred embodiment of the ocular device (100) shown in FIGS. 1A-B. The ocular device (100) comprises a base (102), a pair of supports (120, 170), and a pair of arms (110, 160) connecting the base (102) and the supports (120, 170). The base (102) further comprises a mouthpiece (104) and a guide (106) to center the position of the mouthpiece (104) relative to the subject's bite.

The mouthpiece (104) may optionally be made of a material that is capable of producing and maintaining an imprint of the subject's bite, such as thermoelastomer plastic and other impressionable materials. This will ensure that the position of the ocular device (100) and, more specifically, the position of the supports (120, 170), relative to the subject's eyes will remain consistent upon subsequent use by the subject.

In the preferred embodiment shown in FIGS. 2-3, the object to be inserted onto the subject's eyes by the ocular device (100) is a pair of contact lens (not shown). In this preferred embodiment, the supports (120, 170) are convex-shaped and includes at least one through-hole, slit, depression, or groove (not shown in FIGS. 2-3) to facilitate the removal of the contact lens from the convex support (120, 170) when the contact lens is placed on the subject's eyes.

As further shown in FIGS. 2-3, the arms (110, 160) each comprise a top section (110a, 160a) coupled to the supports (120, 170) and a bottom section (10b, 160b) coupled to the base (102). A joint (111, 161) pivotally connects the top sections (110a, 112a) and the bottom sections (110b, 160b) together such that the top sections (110a, 160a) is angled and may be pivotally movable relative to the bottom sections (110b, 160b) to place the contact lens onto the subject's eyes.

The distance between each of the supports (120, 170) and the base (102) may be adjusted such that when the mouthpiece (104) is placed in the subject's bite and the supports (120, 170) are urged toward the subject's eyes, the object retained by the supports (120, 170) are properly placed onto the subject's eyes.

In one aspect of the preferred embodiment, the arms (110, 160) may each further comprise a threaded bore portion (not shown) that mates with a threaded screw portion (not shown) protruding from the base (102). The distance between the supports (120, 170) and the base (102) may be adjusted by rotating the arms (110, 160) relative to the threaded screw portion protruding from the base (102) in one direction to increase the distance and in the opposing direction to decrease the distance between the supports (120, 170) and the base (102). A stop mechanism (not shown) may optionally be provided to prevent further rotation of the arms (110, 160) when the desired distance between the each of the supports (120, 170) and the base (102) is obtained.

In another aspect of the preferred embodiment, the distance between each of the supports (120, 170) and the base (102) may be slidably adjusted. In this aspect, the arms (110, 160) may each further comprises a bore portion that is slidably positioned over a protruding member that is coupled to the base (102). In this aspect, the arms (110, 160) are slidably moved relative to the protruding members and when a desired distance between the supports (120, 170) is obtained, a bonding agent may be applied to either or both of the bore portion and/or the protruding members.

Figure 4:
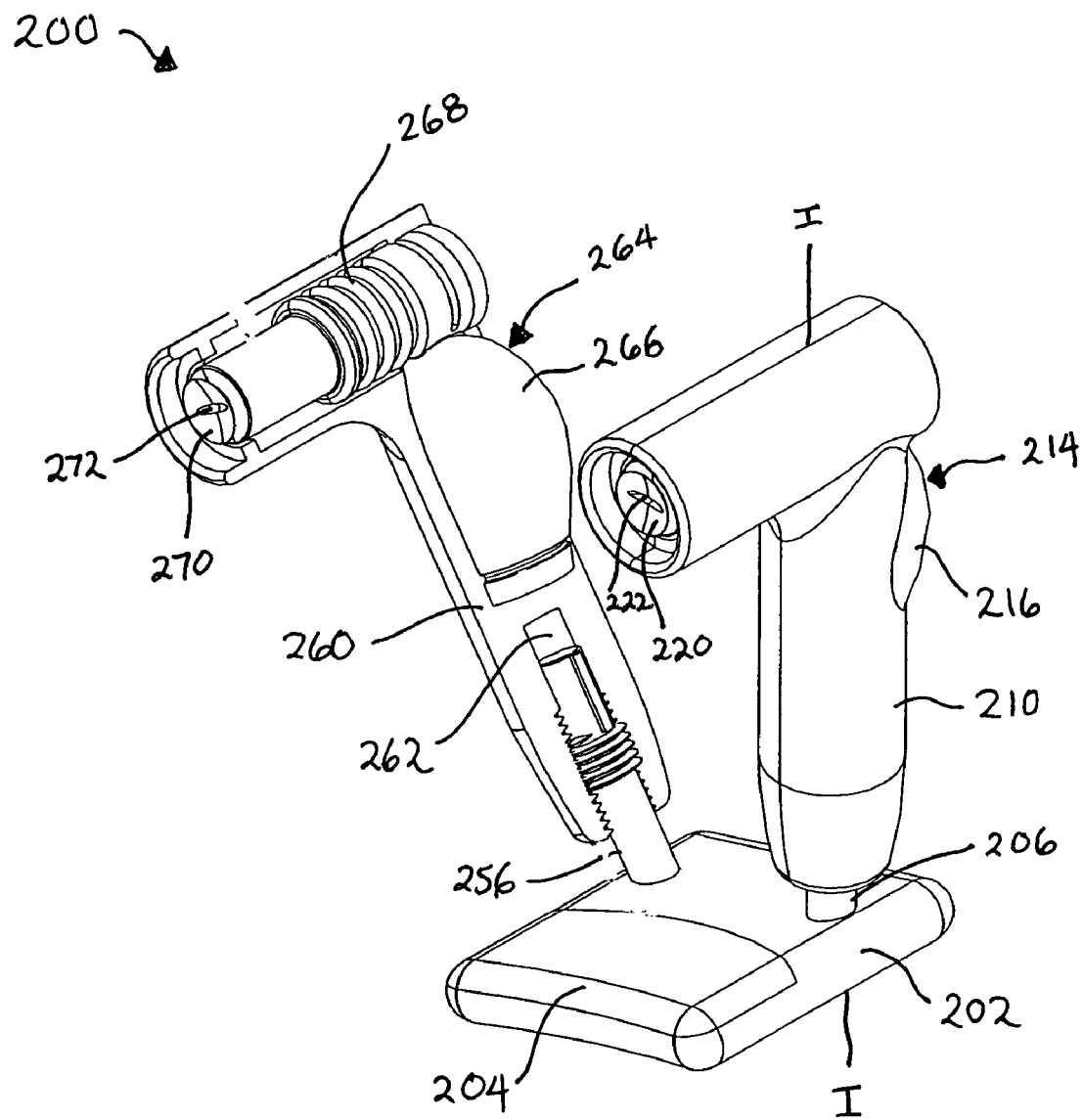
FIG. 4 is a perspective and partial cross-sectional view of another preferred embodiment of the ocular device.
Figure 5:
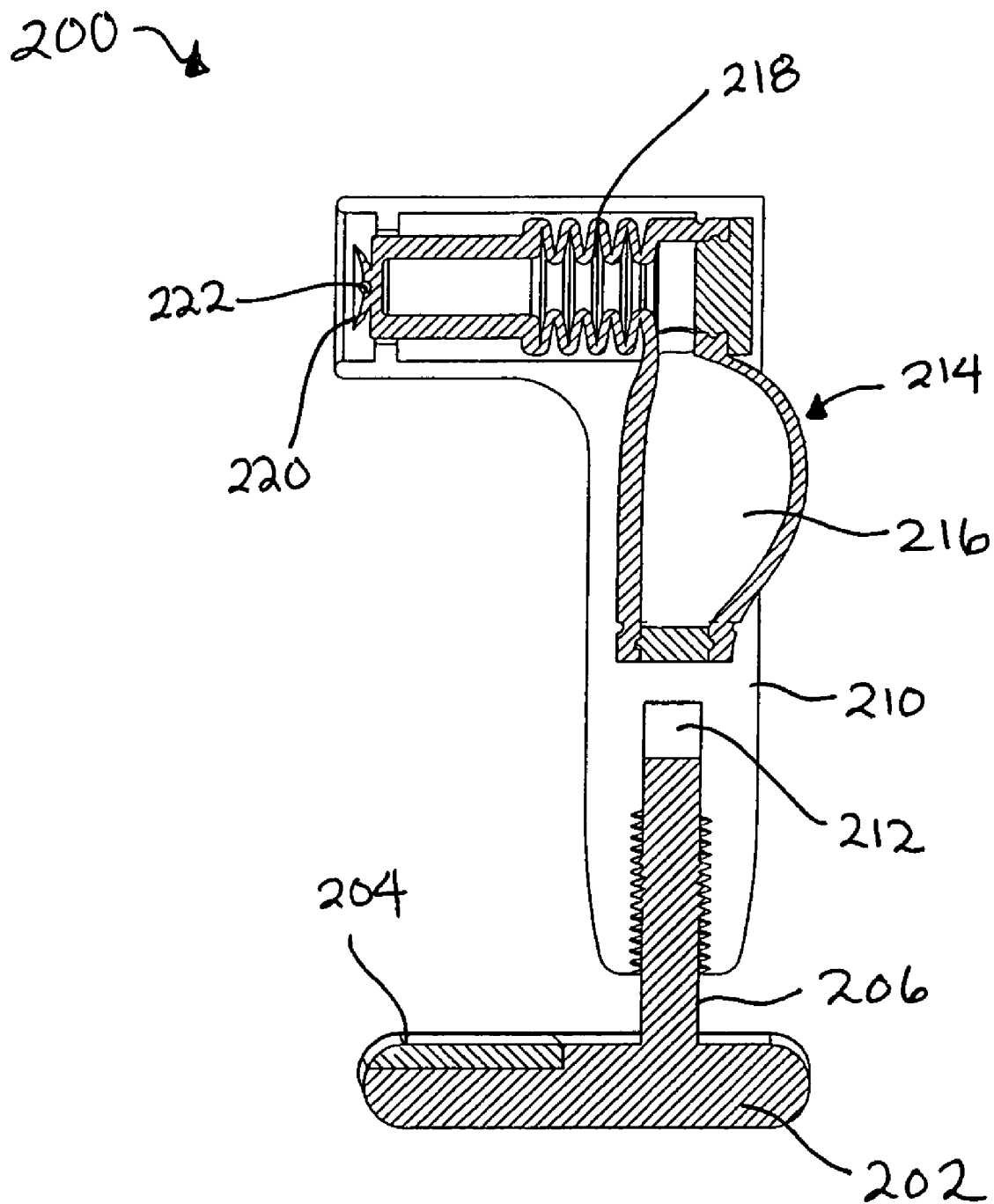
FIG. 5 is a cross-sectional view taken along I-I of FIG. 4.

FIGS. 4-5 illustrate another preferred embodiment of the ocular device (200). The ocular device (200) comprises a base (202) having a mouthpiece (204), expandable chamber assemblies (214, 264), and a housing (210, 260) that couples the expandable chamber assemblies (214, 264) to the base (202) via the threaded screw portions (206, 256) attached to the base (202).

Figure 6:
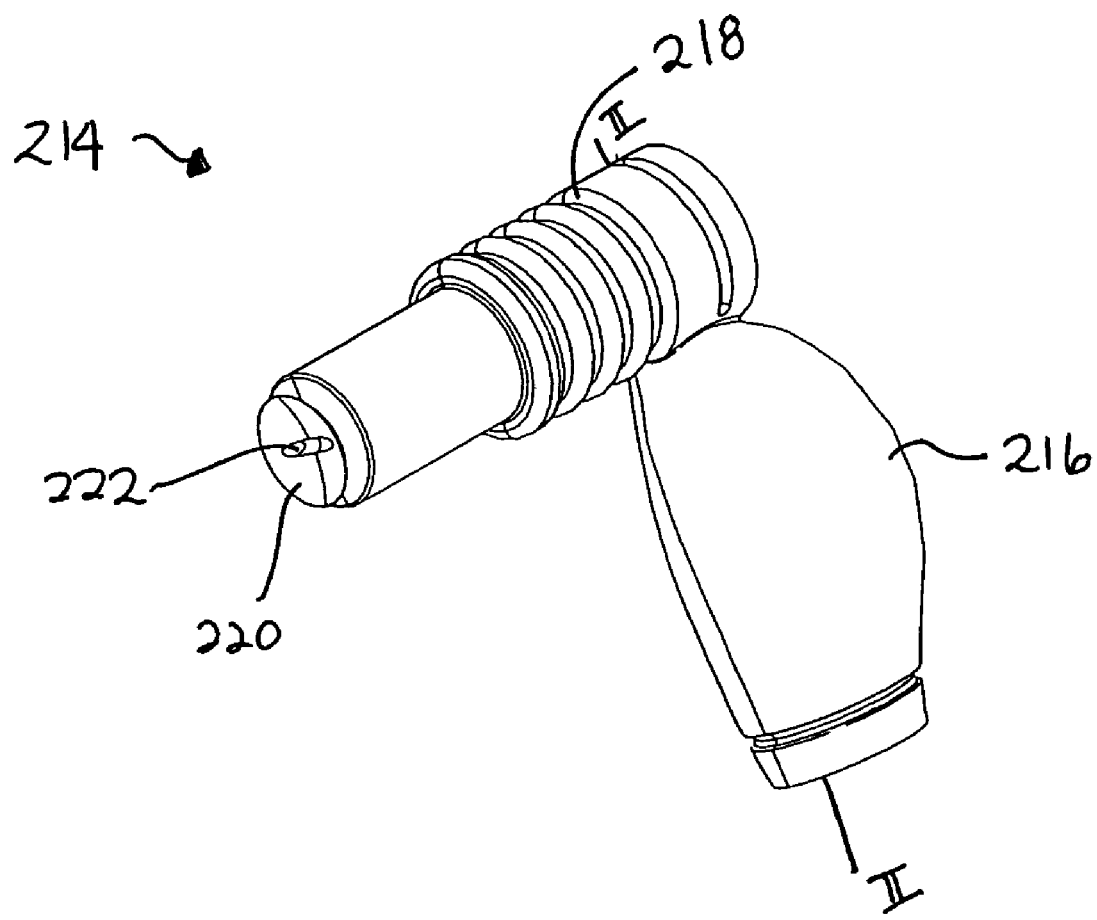
FIG. 6 is a perspective view of the expandable chamber assembly of FIG. 5.
Figure 7:
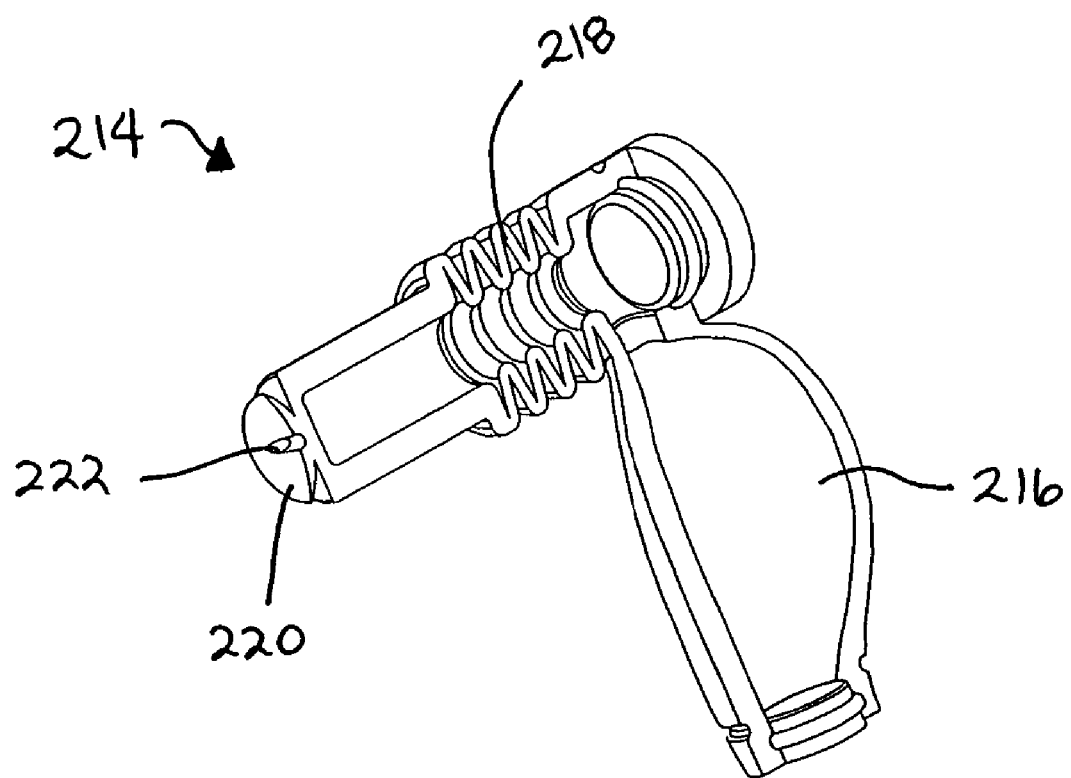
FIG. 7 is a cross-sectional view of the expandable chamber taken along II-II of FIG. 6.
Figure 8:
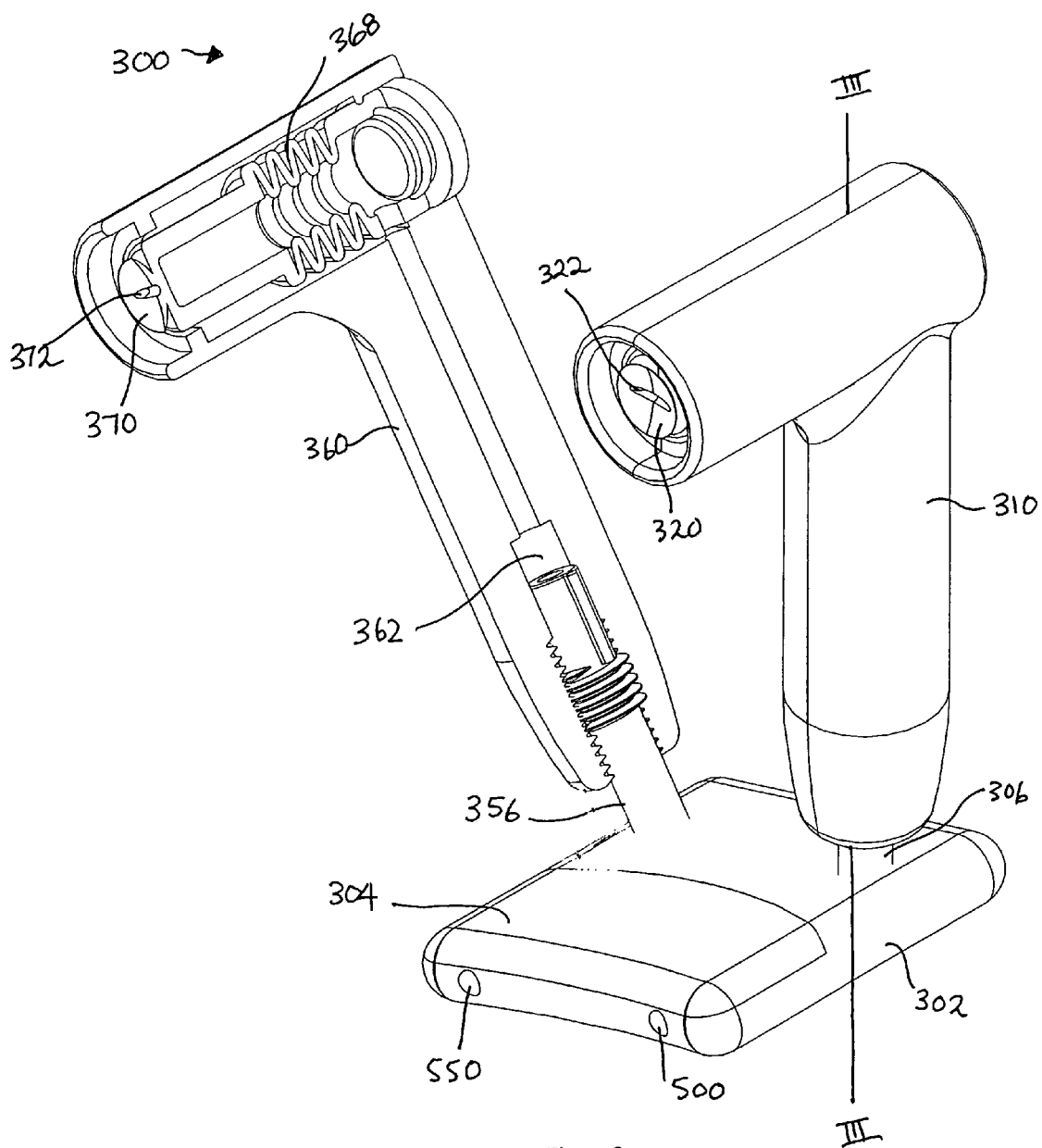
FIG. 8 is a perspective and partial cross-sectional view of a further preferred embodiment of the ocular device.
Figure 9:
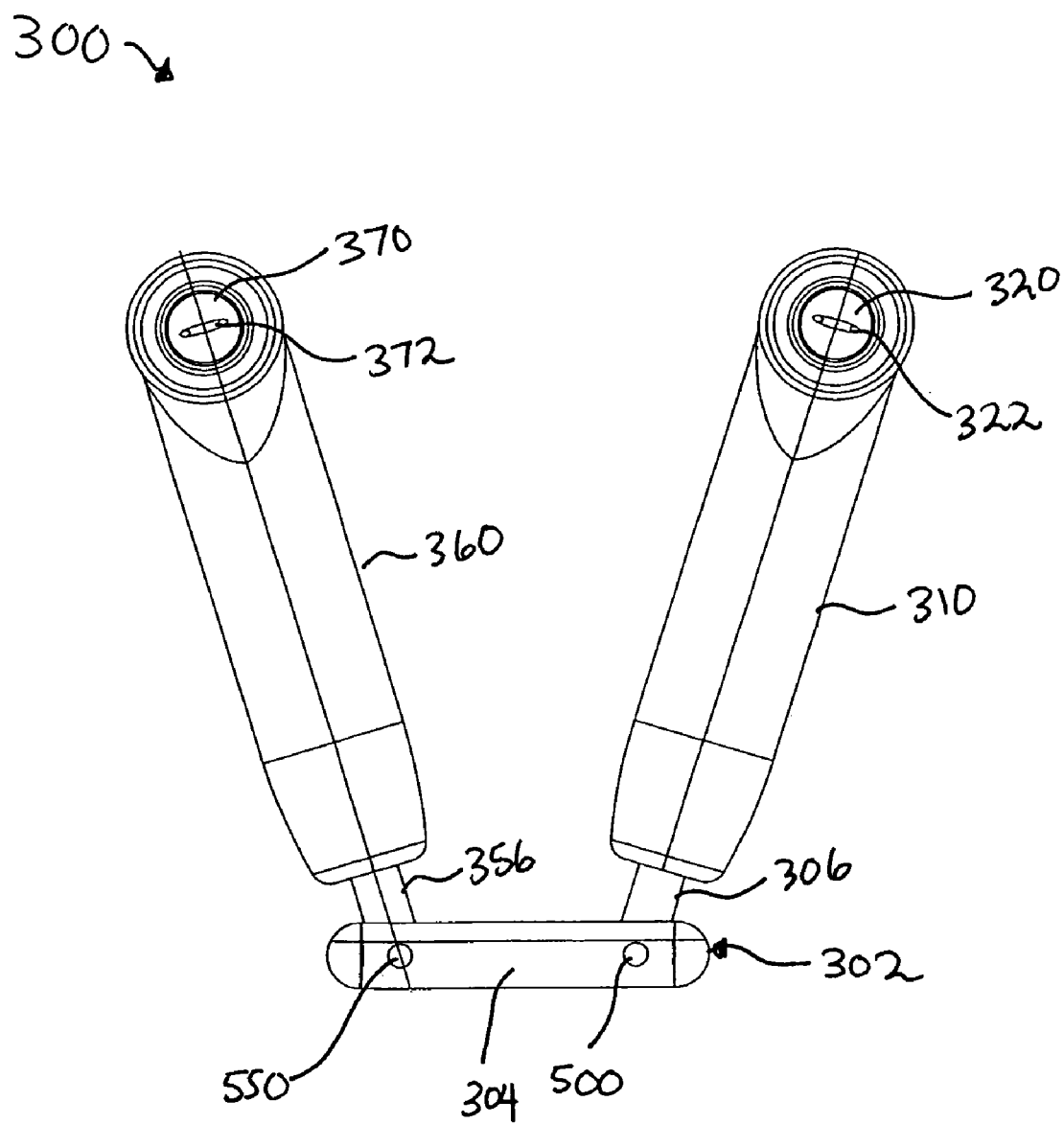
FIG. 9 is a front plan view of the preferred embodiment of FIG. 8.

FIGS. 6-7 shows the expandable chamber assembly (214) in FIGS. 4-5. It should be understood that the ocular device (200) depicted in FIGS. 4-5 contain like parts which are numbered correspondingly. The numbered items in the left side correspond to the numbered items on the right side by adding 50 to the numbers on the right side. Accordingly, the description with respect to the expandable chamber assembly (214) on the right side, as shown in FIGS. 4-5, also applies to the expandable chamber assembly (264) on the left side.

As shown in FIGS. 6-7, the expandable chamber assembly (214) is a closed system comprising a cavity (216), expandable bellows (218), and a support (220). Although the support (220) is depicted as having a convex shape to support a rounded object, such as a contact lens (not shown), it is understood that the support (220) may be configured in any shape necessary to accommodate objects of other shapes which are desired to be placed on the eyes. The support (220) may have a groove or slit (222) to facilitate the removal of the contact lens or other object from the surface of the support (220) once the contact lens is inserted onto the eye.

The cavity (216) and expandable bellows (218) are in fluid communication with each other such that when pressure is applied to the cavity (216), the bellows (218) expands to urge the support (220) out of the housing (210) and insert an object (not shown) retained on the support (220) onto the subject's eyes. The cavity (216) and expandable bellows (218) are substantially hollow and may contain any fluid, such as air, liquid, gel, or any other substance which would permit the bellows (218) to expand in response to pressure that is applied to the cavity (216).

Referring back to FIGS. 4-5, the expandable chamber assemblies (214, 264) are at least partially contained within the housing (210, 260). A portion of the cavity (216, 266) is exposed to permit the application of pressure onto the cavity (216, 266) to expand the bellows (218, 268) and to urge the support (220, 270) towards the eyes to insert the object retained on the support (220, 270) onto the eyes.

Preferably, the supports (220, 270) are each positioned in an area substantially in front of the subject's eyes when the subject bites down on the mouthpiece (204). The ocular device (200) may therefore be configured for each subject's unique facial dimensions, including the vertical distance between the subject's bite and eyes and also the horizontal distance between the subject's eyes. Once configured to a subject's facial dimensions, the ocular device (200) provides consistently reproducible placement of any object to be inserted into the subject's eyes by taking advantage of the fixed distance between the subject's bite and the subject's eyes.

The housing (210, 260) each comprises a threaded bore portion (212, 262) that is adapted to receive and mate with a threaded screw portion (206, 256) coupled to the base (202). The distance between each of the supports (220, 270) and the base (202) may be adjusted by rotating the housing (210, 260) relative to the base (202) in one direction to increase, or in the opposing direction to decrease, the distance between the supports (220, 270) and the base (202). A stop mechanism (not shown) may further be provided to prevent further rotation of the arms (110, 160) and to therefore fix the desired length of the arms (110, 160).

The distance between the two supports (220, 270) may also adjusted to coincide with the distance between the subject's eyes. This may be accomplished by adjusting the angle between the screw portions (206, 256) relative to the base (202) until each of the supports (220, 270) are substantially positioned in front of each eye.

In a preferred embodiment, the screw portions (206, 256) are each coupled to the base (202) by ball and socket joints. Such joints permit rotary movement of the screw portions (206, 256) and therefore the supports (220, 270) in all directions through the movement of a ball in the socket. The distance between the two supports (220, 270) could easily be adjusted to coincide with the distance between the subject's eyes. In addition, the two supports (220, 270) could each independently be adjusted at varying distances away from the subject's face. Once the desired position is obtained, a bonding agent may be applied to the ball and socket joint to fix the position of the supports (220, 270).

FIGS. 8-11 illustrate a further preferred embodiment of the ocular device (300) comprising a base (302) having mouthpiece (304) and a pair of inlet holes (500, 550) disposed in the mouthpiece (304) and a pair of outlet holes (502, 552) disposed on the base (302) in an area outside of the mouthpiece (304). The base (302) further comprises a pair of threaded screw portions (306, 356) configured to receive the threaded bore (312, 362) of a housing (310, 360).

The housings (310, 360) each comprise expandable air bellow assemblies (318, 368) and supports (320, 370) coupled to the bellow assemblies (318, 368). The supports (320, 370) may be convex in shape to accommodate a contact lens. In this embodiment, the supports (320, 370) may include a silt or groove (322, 372) to facilitate the removal of the contact lens from the supports (320, 370) once the contact lens are inserted onto the subject's eyes.

For ease of understanding, only one side of the ocular device (300) will be now be described, since it should be understood that the like parts in the ocular device (300) depicted in FIGS. 8-11 are numbered correspondingly. The numbered items in the left side correspond to the numbered items on the right side by adding 50 to the numbers on the right side. Accordingly, the description with respect to the supports (320) on the right side also applies to the supports (370) on the left side of the ocular device (300).

The ocular device (300) may be used to insert a contact lens or other desired object onto a subject's eyes. As described in the previous embodiments, once the imprint of the subject's bite is created on the mouthpiece (304), the height of the support (320) relative to the base (302) can then be adjusted by rotating the housing (310) relative to the threaded screw portion (306) on the base (302). The support (320) may also be adjusted to be aligned to the center subject's eyes by the threaded screw portion (306) supporting the housing (310).

Figure 10:
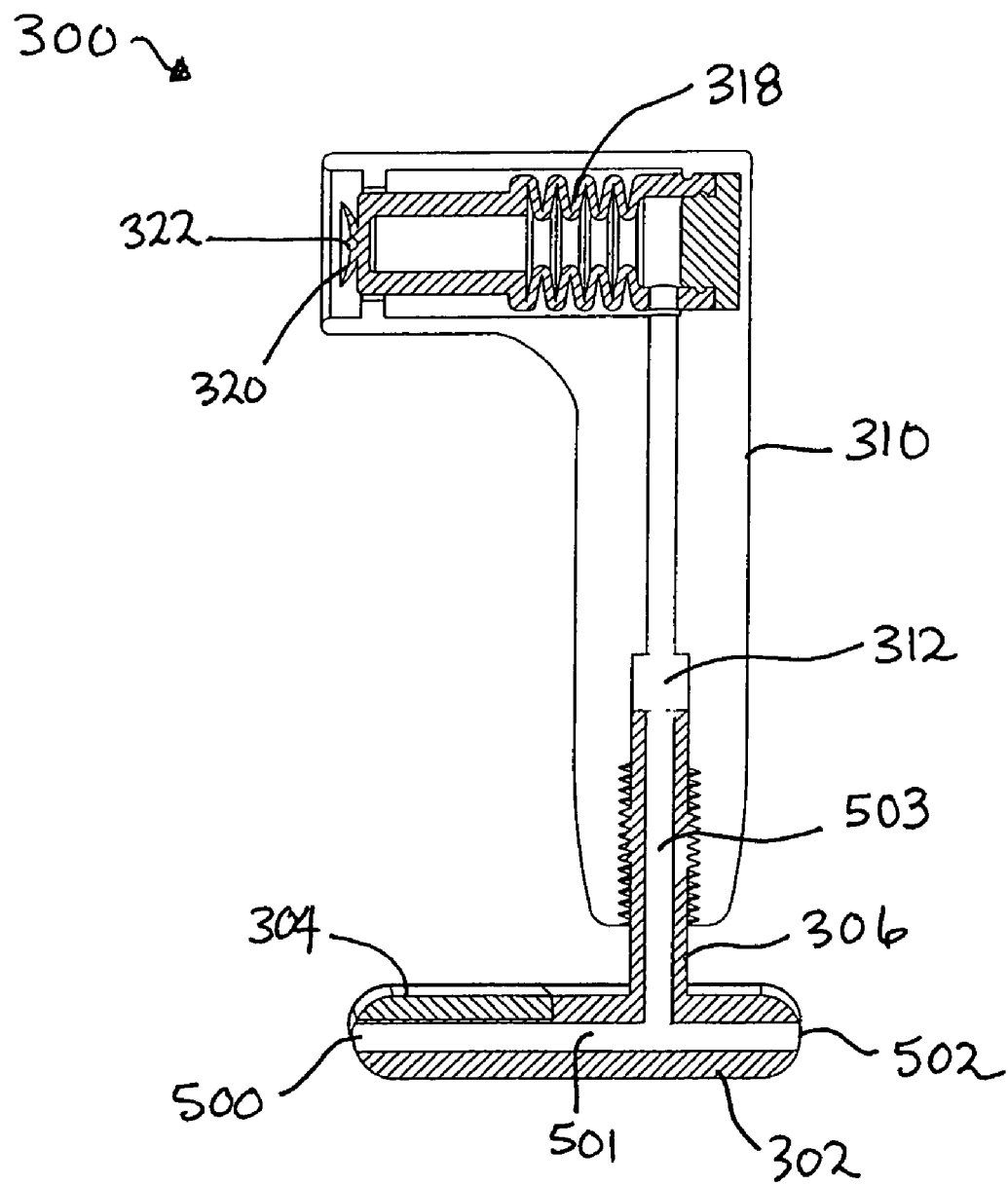
FIG. 10 is a cross-sectional view taken along III-III of FIG. 8.
Figure 11:
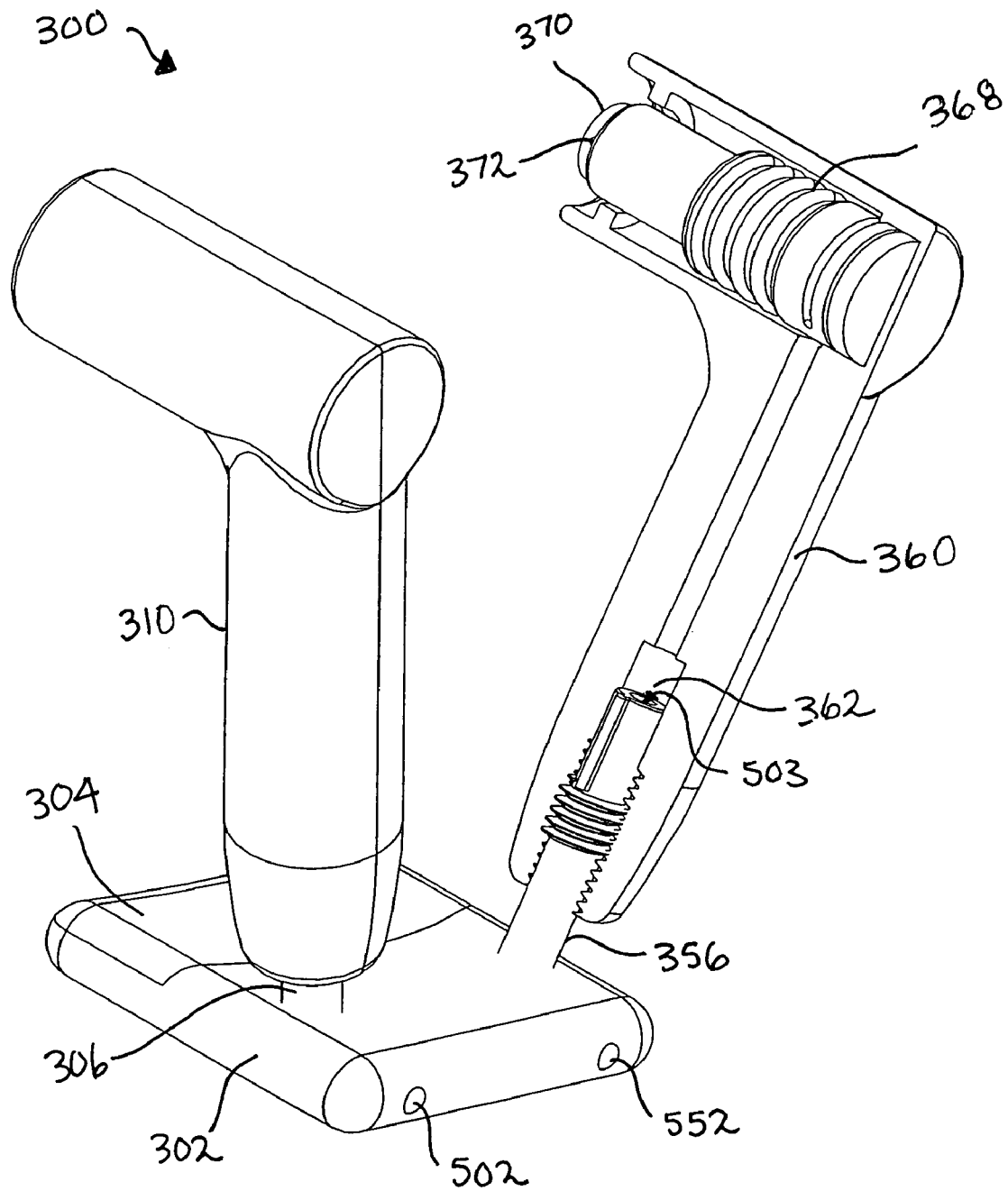
FIG. 11 is a rear perspective and partial cross-sectional view of the preferred embodiment of FIG. 8.

As shown in FIG. 10, the inlet hole (500) is in fluid communication with the outlet hole (502) through a first base conduit (501). The first conduit (501) is also in fluid communication with the expandable air bellow assembly (318) through a first arm conduit (503) that is defined by the hollow channel in the threaded screw portion (306) and the housing (310).

When the outlet hole (502) is not obstructed or covered, air that is expelled into the inlet hole (500) travels through the first base conduit (501) and out of the outlet hole (502). When the outlet hole (502) is obstructed or covered by the subject's finger or a plug, air that is expelled into the inlet hole (500) travels through the first base conduit (501), the first arm conduit (503), and into the expandable air bellow assembly (318) to cause the expandable air bellow (318) to expand and therefore urge the lens support (320) out of the housing (310) and onto the subject's eye.

Although not shown in FIG. 10, the inlet hole (550) is in fluid communication with the outlet hole (552) through a second base conduit (not shown) which, in turn, is in fluid communication with the expandable air bellow assembly (368) through a second arm conduit defined by the hollow channel in the threaded screw portion (356) and housing (360). Accordingly, when the outlet hole (552) is not obstructed or covered, air that is expelled into the inlet hole (502) travels through the second base conduit and out of the outlet hole (552).

Other configurations for the inlet and outlet holes, not shown in FIGS. 8-11, are contemplated.

Figure 12:
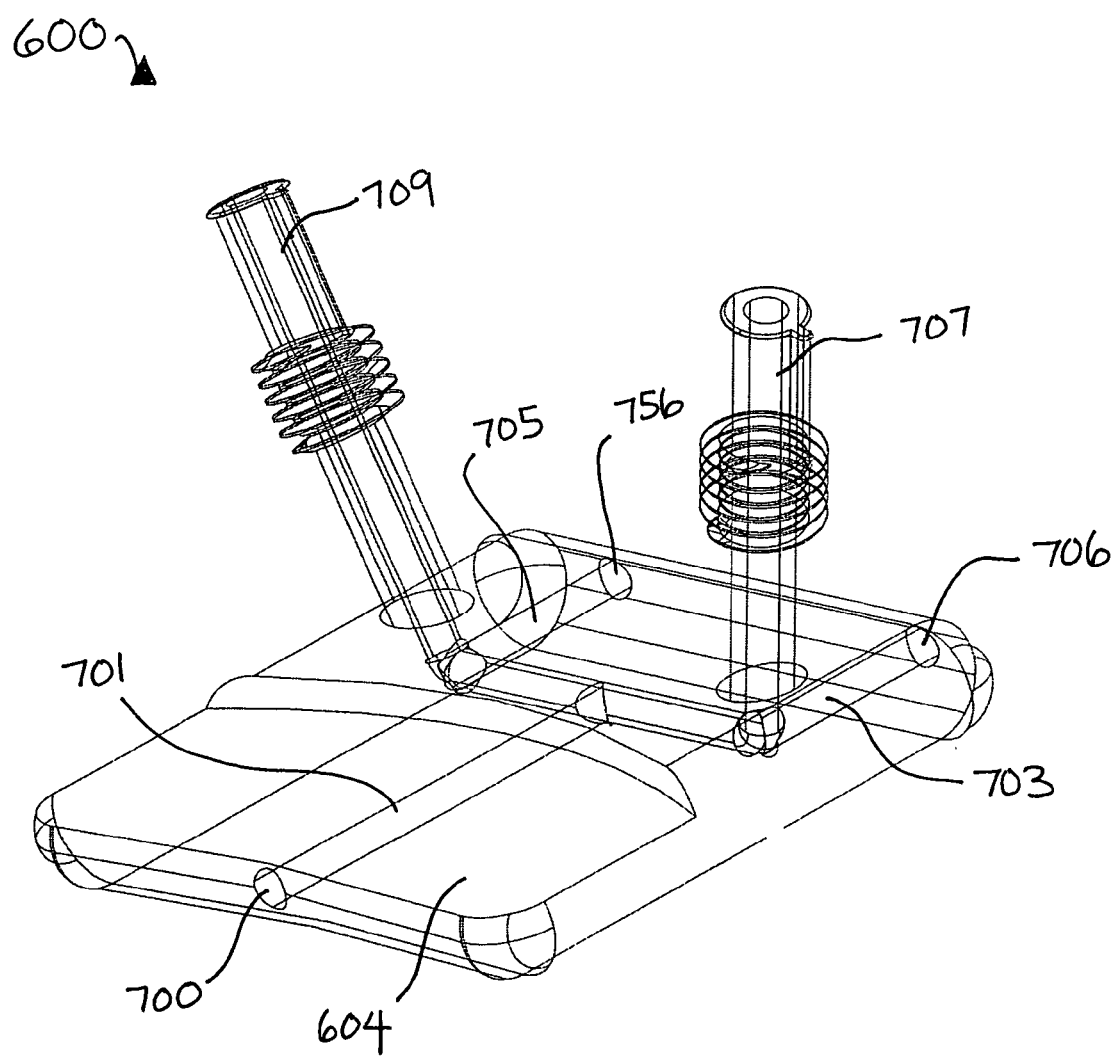
FIG. 12 is a perspective view of the base for yet a further preferred embodiment of the ocular device.

FIG. 12 is a perspective view of the base (600) for yet a further preferred embodiment of the ocular device. FIG. 12 shows yet another aspect of the preferred embodiment in which the base (600) comprises a mouthpiece (604) having one inlet hole (700). The inlet hole (700) is in fluid communication with first and second outlet holes (706, 756) through an inlet conduit (701) disposed in the base (600) and leading to a first and second conduits (703, 705) which connect to the first and second outlet holes (706, 756), respectively. The first and second conduits (703, 705) are also in fluid communication with first and second arm conduits (707, 709) that lead to the expandable air bellow assemblies (not shown).

In the preferred embodiment depicted in FIG. 12, the supports that are coupled to the air bellow assemblies (not shown) may be selectively be deployed by covering one of the outlet holes (706, 756) while air is being introduced into the inlet hole (700). Alternatively, both supports may be deployed at the same time by introducing air into the inlet hole while covering both outlet holes (706, 756).

In another aspect of the preferred embodiment, not shown in the Figures, the base may comprise two inlet holes and a single outlet hole. In this preferred embodiment, air may be selectively blown into one of the two inlet holes to selectively deploy one of the supports. A tongue or a plug may be used to block one of the inlet holes while air is being blown in the other inlet hole. Alternatively, both supports may be deployed at the same time by introducing air into both inlet holes while covering the outlet hole.

It is understood that the ocular device described herein is not limited to use in connection with the insertion of contact lens. Rather, the ocular devices described herein have broad applicability with respect to any object that is to be inserted onto the eye. The ocular devices may be adapted to such other devices by changing the shape and configuration of the supports. The ocular devices may also be used in connection with the delivery of medication to the eyes, patch, cream, saline solution, eye drops, liquid or other objects.

Figure 13:
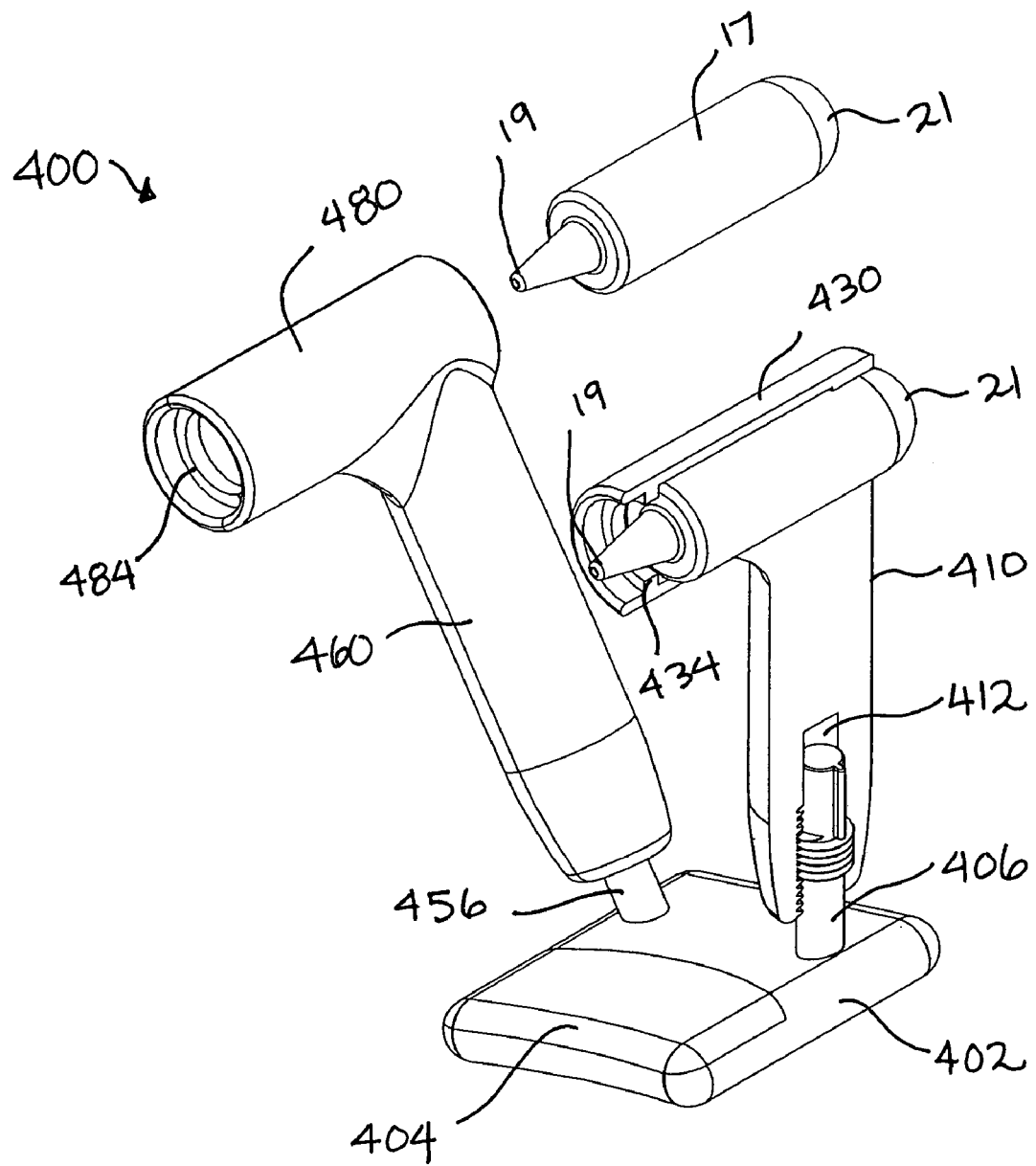
FIG. 13 is a perspective and partial cross-sectional view of yet a further embodiment of the ocular device.

FIG. 13 shows yet a further preferred embodiment of an ocular device (400) that adapted to deliver medication (17) to the subject's eyes. The ocular device (400) comprises a base (402) having a mouthpiece (404) and a pair of threaded screw portions (406, 456) and a pair of housing members (410, 460)

comprising threaded bore portions (412, 462 not shown) adapted to receive the threaded screw portions (406, 456).

The housing members further comprise a receptacle head (430, 480) that is adapted to receive and hold a cartridge or container of medicine (17). The receptacle heads (430, 480) each comprise a open back through which the medicine (17) may be inserted. The receptacle heads (430, 480) each further comprises a stop support (434, 484), which is depicted in FIG. 13 as a rim that protrudes around the interior periphery of the receptacle head (430, 480) to prevent the medicine from sliding out of the receptacle head (430, 480).

The medication bottles (17) are slidably inserted into the receptacle heads (430, 480) through the opening in the rear of the receptacle heads (430, 480). The medication bottles (17) preferably comprises a dispensing tip (19) to dispense the medication (17) onto the subject's eyes and a removable plastic cap (not shown) to protect the dispensing tip (19).

In one aspect of the preferred embodiment, the medication bottles (17) also comprises a bladder (21), such that applying pressure to the bladder (21) will cause the medication to dispense out of the container (17) and onto the subject's eyes.

In another aspect of the preferred embodiment, medication is dispensed from the container by gravity when the subject's head is in an at least partially horizontal position. In this aspect, no pressure need to be applied to the container (17) to cause the medication to dispense out of the container (17) and onto the subject's eyes.

In a particularly preferred embodiment, the ocular device (400) is customized for each subject's unique facial dimensions, including the distance between the subject's bite and each of the subject's eyes and also the distance between the subject's eyes. Once customized, the ocular device (400) provides consistently reproducible insertion of the medication (17) contained in the receptacle head (430, 480) by taking advantage of the fixed distance between the subject's bite and the subject's eyes.

In the particularly preferred embodiment depicted in FIG. 13, the base comprises a mouthpiece (404) that is made of a material that is capable of retaining a permanent impression of the subject's bite. Non-limiting examples of such material include thermoelastiomer plastic and other impressionable materials. Once a permanent impression of the subject's bite is made on the mouthpiece (404), the orientation of the subject's bite on the mouthpiece (404) is stabilized and consistent upon subsequent use.

The distance between the receptacle heads (430, 480) and the base (402) may be adjusted such that the medication (17) contained in the receptacle heads (430, 480) will be inserted into each of the subject's eyes.

It is understood that the ocular device (400) may be designed to accommodate medication in containers of various shapes and sizes. For example, the ocular device (400) may comprise, instead of the receptacle heads (430, 480), other securing apparatus, such as clamps or clips, to attach any container in place.

The invention described and claimed herein is not to be limited in scope by the specific preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The invention claimed is:

1. An ocular device to facilitate the positioning and insertion of an object onto a subject's eyes, the device comprising:
   a base comprising a mouthpiece; and
   at least one support coupled to the base and configured to releasably retain the object;
   wherein the support is adjustably configured to be positioned at a fixed distance from the base; and
   wherein the base anchors the position of the support relative to the subject's eyes when the mouthpiece is placed between the subject's teeth such that displacement of the support toward the subject's eyes reproducibly places the object onto the subject's eyes.

2. The ocular device of claim 1, wherein the mouthpiece is made of a material that is capable of producing a permanent imprint of the subject's bite.

3. The ocular device of claim 2, wherein the mouthpiece comprises a thermoelastomer plastic.

4. The ocular device of claim 1, wherein the mouthpiece is removably attached to the base and comprises a pre-formed groove to accommodate the subject's bite.

5. The ocular device of claim 1 wherein the base comprises a guide to center the placement of the mouthpiece relative to the subject's bite.

6. The ocular device of claim 1, wherein the object is a contact lens.

7. The ocular device of claim 6, wherein the support comprises a convex surface to releasably retain the contact lens.

8. The ocular device of claim 7, wherein the convex surface includes at least one through-hole to facilitate the removal of the contact lens from the convex surface when the contact lens is placed on the subject's eye.

9. The ocular device of claim 7, wherein the convex surface includes at least one depression or groove to facilitate the removal of the contact lens from the convex surface when the contact lens is placed on the subject's eye.

10. The ocular device of claim 1 comprising two supports.

11. The ocular device of claim 10, wherein the device comprises two arms, the two arms each coupling one support to the base and the two arms each having lengths.

12. The ocular device of claim 11, wherein the length of each arm is separately adjustable to position each of the two supports at a distance from the base such that the supports are located in an area substantially in front of the subject's eyes when the mouthpiece is placed between the subject's teeth.

13. The ocular device of claim 11, wherein the two arms each further comprise a bore portion and wherein the base further comprises two threaded screw portions, wherein the bore portions are each configured to receive the threaded screw portions and wherein the length of each arm is adjusted by rotating the bore portion relative to the threaded screw portion.

14. The ocular device of claim 13, wherein the arms each have a stop lock to prevent further rotation of the bore portion and to fix the desired length of the arm.

15. The ocular device of claim 13, wherein the threaded screw portions are coupled to the base.

16. The ocular device of claim 15, wherein the distance between the supports may be adjusted to coincide the distance between the subject's eyes.

17. The ocular device of claim 16, the supports may be adjusted at a desired distance away from the face.

18. The ocular device of claim 11, wherein the two arms are at least partially flexible.

19. The ocular device of claim 11, wherein the two arms each comprise a top section coupled to the support and a bottom section coupled to the base, wherein the top and bottom sections are pivotally connected by a joint such that the top sections may be pivotally movable with respect to the bottom section.

20. The ocular device of claim 19, wherein the two supports are urged towards the subject's eyes to insert the object on the subject's eyes.

21. A method for inserting an object onto the eyes, the method comprising:
provide the ocular insertion device of claim 1;
placing the object to be inserted onto the eyes on the support;
biting the mouthpiece; and
pushing the support toward the eyes to contact the object onto the eyes.

22. An ocular device for facilitating the positioning and insertion of an object onto a subject's eyes, the device comprising:
a base comprising a mouthpiece configured to be maintained in the subject's bite;
at least one support adjustably configured to be positioned in front of the subject's eyes when the mouthpiece is maintained in the subject's bite;
an expandable chamber assembly coupled to the support;
wherein the expandable chamber assembly expands to urge the support toward the subject's eyes to insert the object onto the subject's eyes when
pressure is applied to the expandable chamber assembly.

23. The ocular device of claim 22 wherein the object is a pair of contact lens.

24. The ocular device of claim 23 comprising two supports, the two supports each configured to releasably retain one of a pair of contact lens.

25. The ocular device of claim 24, wherein the expandable chamber assemblies each further comprises bellows and a cavity, wherein each of the supports are coupled to the bellows.

26. The ocular device of claim 25, wherein the bellows and the cavity are in fluid communication with one another.

27. The ocular device of claim 26, wherein the bellows each expands to urge the supports toward the subject's eyes to insert the contact lens onto the subject's eyes when pressure is applied to the cavity.

28. The ocular device of claim 27, wherein the bellows and supports are positioned on a first at least partially horizontal plane and the cavity is positioned on a second at least partially vertical plane, wherein the first plane is substantially perpendicular to the second planes.

29. The ocular device of claim 28 further comprising a pair of housings each coupling the supports to the base, wherein the housings each have lengths that are separately adjustable to position each of the lens supports in an area substantially in front of the subject's eye when the mouthpiece is placed between the subject's teeth.

30. The ocular device of claim 29, wherein the angle defined by each of the housings and the base is adjustable to position the lens support substantially at the center of the subject's eye when the mouthpiece is placed between the subject's teeth.

31. The ocular device of claim 26, wherein the bellows and the cavity contain air.

32. The ocular device of claim 26, wherein the bellows and cavity contain a liquid.

33. A method for inserting an object onto the eyes, the method comprising:
providing the ocular insertion device of claim 22;
placing the object to be inserted onto the eyes on the support;
biting at least a portion of the base; and
applying pressure to the expandable chamber assembly to insert the object onto the eyes.

34. An ocular device for facilitating the positioning and insertion of an object onto a subject's eyes, the device comprising:
a base comprising a mouthpiece and at least one inlet hole disposed in the mouthpiece;
a first and second supports coupled to the base and configured to releasably retain the object, the first and second supports each having an expandable chamber in fluid communication with the at least one inlet hole;
wherein the first and second supports are actuated towards the subject eyes when air is blown into the inlet hole;
wherein the first and second supports are each adjustably configured to be positioned at a fixed distance from the base; and
wherein the base anchors the position of the supports when the mouthpiece is placed between the subject's teeth such that actuation of the first and second supports toward the subject's eyes reproducibly places the object onto the subject's eyes.

35. The ocular device of claim 34 comprising a first and second inlet holes, wherein the first and second inlet holes each separately actuates the first and second supports, respectively, when air is blown into either or both of the first and second inlet holes.

36. The ocular device of claim 35 further comprising at least one outlet hole disposed on the base, wherein the outlet hole is in fluid communication with the first and second inlet holes and first and second supports are actuated by the expandable chambers when air is blown into the first and second inlet holes and the outlet hole is covered.

37. The ocular device of claim 36, wherein the outlet hole is covered by the subject's finger.

38. The ocular device of claim 34 comprising one inlet hole.

39. The ocular device of claim 38 further comprising a first and second outlet holes, wherein the first and second outlet holes are in fluid communication with the inlet hole.

40. The ocular device of claim 39, wherein the first and second outlet holes are separately in fluid communication with the expandable chambers for the first and second supports, respectively.

41. The ocular device of claim 40, wherein the first and second supports are separately actuated by selectively covering either one or both of the first and second outlet holes when air is blown into the inlet hole.

42. The ocular device of claim 41, wherein the outlet hole is covered by the subject's finger.

43. A method for inserting an object onto the eyes, the method comprising:
providing the ocular insertion device of claim 34;
placing the object to be inserted onto the eyes on the support;
biting at least a portion of the mouthpiece and forming a seal around the mouthpiece with the lips;
blowing air into the inlet hole disposed in the mouthpiece to actuate the supports towards the eyes; and
contacting the object onto the eyes.

44. An ocular device to facilitate the administration of medication onto a subject's eyes, the device comprising:
a base comprising a mouthpiece;
at least one receptacle head coupled to the base and configured to store medication;

wherein the receptacle head is adjustably configured to be positioned at a fixed distance from the base and substantially in front of the subject's eyeball; and wherein the base anchors the position of the receptacle head relative to the subject's eyes when the mouthpiece is placed between the subject's teeth.

45. The ocular device of claim 44, wherein the medication is provided in a container that is configured to be retained by the receptacle head.

46. The ocular device of claim 45, wherein the container comprises a dispensing tip and a bladder.

47. The ocular device of claim 46, wherein pressure applied to the bladder causes the medication to be discharged out of the dispensing tip.

48. The ocular device of claim 47, wherein the container and the receptacle head are cylindrically-shaped and wherein the receptacle head comprises open front and rear ends.

49. The ocular device of claim 48 wherein the container is inserted into the receptacle head through the open rear end of the receptacle head and wherein the open front end of the receptacle head further comprises a rim that protrudes around the interior periphery of the receptacle head to secure the container within the receptacle head.

50. The ocular device of claim 45, wherein the medication is dispensed from the container by gravity.

51. A method for administering medication onto the eyes, the method comprising:
providing the ocular device of claim 44;
providing a container of medication in the receptacle head;
biting at least a portion of the mouthpiece; and
applying pressure onto the container to discharge the medication from the receptacle head and onto the eyes.

52. An ocular device to facilitate the positioning and insertion of objects onto a subject's eyes, the device comprising:
a mouthpiece that is held between the subject's teeth;
two supports coupled to the mouthpiece and each support removably retaining a single one of the objects to be inserted onto the subject's eyes;
wherein the supports are adjustably configured to be positioned at a fixed distance from the mouthpiece; and
wherein the mouthpiece anchors the position of the supports relative to the subject's eyes when the mouthpiece is held between the subject's teeth.

53. The ocular device of claim 52, wherein the object is contact lens.

54. The ocular device of claim 52, wherein the object is medication.

55. The ocular device of claim 52 further comprising arms coupling the supports to the mouthpiece.

56. The ocular device of claim 55, wherein the lengths of the arms are each slidably adjustable.

57. The ocular device of claim 56, wherein the lengths of the arms are each fixed by applying a bonding agent to the slidably adjustable arms.

58. An ocular device to facilitate the positioning and insertion of an object onto a subject's eyes, the device comprising:
mouthpiece means held in position in the subject's bite;
support means coupled to the mouthpiece means for releasably maintaining an object to be inserted onto the subject's eyes; and
actuating means for displacing the support means towards the subject's eyes to insert the object onto the subject's eyes;
wherein the support means are adjustably configured to be positioned at a fixed distance from the mouthpiece means; and
wherein the mouthpiece means anchors the position of the support means relative to the subject's eyes when the mouthpiece means is placed between the subject's teeth, such that the object is reproducibly placed onto the subject's eyes when the actuating means displaces the support means towards the subject's eyes.

59. The ocular device of claim 58 further comprising a first adjustment means to adjust the distance between the mouthpiece means and the support means.

60. The ocular device of claim 59 further comprising a second adjustment means to adjust the distance between the support means.

61. The ocular device of claim 60 wherein the second adjustment means further comprises a second stop means to fix the distance between the support means.

62. The ocular device of claim 59 wherein the first adjustment means further comprises a first stop means to fix the distance between the support means and the mouthpiece means.

* * * * *